United States Patent [19]

Ikeuchi et al.

[11] Patent Number: 5,387,403
[45] Date of Patent: Feb. 7, 1995

[54] AUTOMATIC STERILIZING APPARATUS

[75] Inventors: Hiroshi Ikeuchi, Ashiya; Yoshinari Iwamura, Kobe; Akira Kawayoshi, Nishiwaki; Shoji Hida, Suita, all of Japan

[73] Assignee: H. Ikeuchi & Co., Ltd., Osaka, Japan

[21] Appl. No.: 76,849

[22] Filed: Jun. 15, 1993

[51] Int. Cl.$^6$ .............................. A61L 2/00
[52] U.S. Cl. ................... 422/292; 239/161; 239/162; 422/300; 422/305
[58] Field of Search ............ 422/292, 300, 305; 239/160, 161, 162, 172; 134/166 R, 200, 170

[56] References Cited

U.S. PATENT DOCUMENTS

| | | | |
|---|---|---|---|
| 2,516,401 | 7/1950 | Marcuse | 422/28 X |
| 2,587,240 | 2/1952 | Spreng | 239/161 X |
| 2,643,155 | 6/1953 | Wright et al. | 239/160 X |
| 2,722,453 | 11/1955 | Moore | 239/162 |
| 3,816,074 | 6/1974 | Decupper | 422/305 |
| 4,414,037 | 11/1983 | Friedheim | 422/305 |
| 4,552,728 | 11/1985 | Taylor | 422/300 |
| 4,601,886 | 7/1986 | Hindgins | 422/116 |
| 4,783,008 | 11/1988 | Ikeuchi et al. | 239/421 |
| 4,988,485 | 1/1991 | Bene | 422/292 |

Primary Examiner—Robert J. Warden
Assistant Examiner—Krisanne M. Thornton
Attorney, Agent, or Firm—Wenderoth, Lind & Ponack

[57] ABSTRACT

A sterilizing apparatus installed on a car includes a nozzle-installing pipe on which a plurality of nozzles are mounted at regular intervals, a driving mechanism for varying the spray angles of the nozzles, a driving mechanism for controlling the spray time periods, a supply mechanism for supplying disinfectant to a disinfectant-flowing path equipped in the nozzle-installing pipe, a plurality of tanks containing disinfectant to be supplied to the supply mechanisms and control mechanisms for controlling the operation of the driving mechanisms. The car is moved to a required place in a hospital, and the nozzles are operated by spray disinfectant particles, the diameter of which are 10 μm or less.

12 Claims, 17 Drawing Sheets

Fig. 16(A)

upper shelf 1.6m survival rate of bacteria distance from the nozzle

Fig. 16(B)

intermediate shelf 0.9m survival rate of bacteria distance from the nozzle

Fig. 17(B)

intermediate shelf survival rate of bacteria distance from the nozzle 0.00m   0.29m   0.57m   0.86m   1.14m   1.43m   1.17m   2.00m

Fig. 17(c)

lower shelf survival rate of bacteria distance from the nozzle 0.00m   0.29m   0.57m   0.86m   1.14m   1.43m   1.17m   2.00m

Fig. 18(A)

upper shelf survival rate of bacteria 0.00m  0.29m  0.57m  0.86m  1.14m  1.43m  1.17m  2.00m   distance from the nozzle

Fig. 18(B)

intermediate shelf survival rate of bacteria 0.00m  0.29m  0.57m  0.86m  1.14m  1.43m  1.17m  2.00m   distance from the nozzle

Fig. 18(c)

AUTOMATIC STERILIZING APPARATUS

BACKGROUND OF THE INVENTION

1. Field of the Invention

The present invention relates to a method and an apparatus for automatically sterilizing bacteria in a hospital, and more particularly to the method and the apparatus for effectively sterilizing bacteria by spraying disinfectant so as to prevent the occurrence of an infection caused by bacteria floating in an operation room, a ward or the like of a hospital or bacteria which have stuck to walls or floors of the hospital. The method and apparatus can also be used in equipment such as in a food manufacturing factory requiring sterilization.

2. Description of the Related Art

Recently, hospital infection has been remarkably increasing. When babies, old people or people suffering from disease having a weak resistance to bacteria become infected with Pseudomonas aeruginosa or MRSA (Methicillin Resistant Staphylococcus aureus) having multiple drug resistance to antibiotics, bacteria increase in their bodies, thus causing pneumonia, enteritis, suppuration of skin or septicemia.

Since MRSA is resistant to antibacterial agents in addition to antibiotics, research is being conducted to develop medicine or methods for sterilizing MRSA. In this situation, it is necessary to sterilize bacteria in hospitals so as to prevent people from being infected with MRSA or the like.

MRSA grows in the highest degree in operating rooms. According to a sampling inspection carried out recently, positive MRSA was 0 to 3% in wards for internal treatment while it was as high as 20% in wards for surgical treatment.

It is therefore absolutely necessary to completely sterilize bacteria in operating rooms to prevent the hospital infection. MRSA of a patient may be infected via a patient's bed, clothes of doctors, nurses, or workers, air-conditioning equipments or medical instruments not sterilized sufficiently. Accordingly, it is also necessary to sterilize places in which MRSA is likely to grow in addition to operating rooms.

It is necessary to sterilize bacteria which have stuck to floors, walls, ceilings, beds, shelves, medical equipments and those floating in the air.

Mops on which disinfectant has been put are mainly used to wipe floors or the like to sterilize bacteria which have stuck thereto. Bacteria floating in the air is sterilized by disinfectant which is scattered or sprayed; gas fumigation; ultraviolet rays irradiated to floors or the like; or filters of air-conditioning equipment.

The above-described sterilizing methods have the following problems:

1. A sterilizing method which uses a mop for cleaning has a problem in that the mop may not be clean. Since mops are made of cotton, bacteria tend to stick thereto. For example, approximately as many as 50,000 to 100,000 bacteria stick thereto per one inch. That is, mops may scatter bacteria over a large area.

It is difficult to adjust the concentration of disinfectant to be provided to the mop to an appropriate value. In addition, an excessive amount of disinfectant may be contained in the mop and thus disinfectant may not be applied uniformly to floors or the like.

Further, it often occurs that a high place or the back surface of a shelf or the like is not wiped with the mop. In addition, a sterilizing method is also required to sterilize bacteria floating in the air.

2. In the sterilization by means of gas fumigation to be carried out with a room air-tight, the room smells of gas for a few days after the room is fumigated.

3. In the sterilization by means of ultraviolet rays, portions of the room shaded from the ultra-violet rays cannot be sterilized. The sterilizing effect decreases in proportion to the square of the distance between an object and a light source. Thus, floors, ceilings or the like cannot be uniformly sterilized. Further, resin or products made of rubber will tend to deteriorate.

4. In the sterilization by means of the filter of air-conditioning equipment, bacteria floating in the air can be caught but bacteria which have stuck to floors or the like cannot be sterilized. Therefore, an additional sterilizing method is also required to sterilize bacteria stuck to floors or the like. Moreover, it is necessary to replace the filter often.

5. The method of scattering or spraying disinfectant is the most effective because the method is capable of sterilizing bacteria floating in the air and bacteria which have stuck to floors and the like.

The method has, however, a problem that large-diameter particles of disinfectant drop to the floor before they sterilize bacteria floating in the air, hence causing a decrease in the sterilizing effect of the disinfectant.

It is necessary to uniformly spray disinfectant in all directions in the room. It takes much time to spray disinfectant manually. In addition, a person in charge may be infected with bacteria while the person is spraying the disinfectant. In addition, there is a great possibility that ill effects will be produced.

SUMMARY OF THE INVENTION

It is an object of the present invention to provide an apparatus and a method for automatically spraying disinfectant in the form of particles, the average diameter of which is 10 $\mu$m or less.

It is another object of the present invention to provide an apparatus and a method for allowing particles to stay in the air for a long time to efficiently sterilize bacteria floating in the air.

It is still another object of the present invention to provide an apparatus and a method for spraying disinfectant even after the air of a space is saturated with droplets of disinfectant so that particles drop and stick to floors, ceilings and the top and bottom surfaces of medical equipment, thus wetting them and sterilizing bacteria which have stuck thereto.

In accomplishing these and other objects of the present invention, there is provided an automatic sterilizing apparatus installed on a car which is moved to a required place in a hospital so as to spray disinfectant, comprising: a disinfectant-supply tank containing disinfectant; compressed air-supply means; a plurality of nozzles, comprising twin heads, for spraying a mixture of disinfectant supplied from the disinfectant-supply tank and compressed air supplied from the compressed air-supply means in the form of particles, the average diameter of which is 10 μm or less a nozzle-installing pipe on which the nozzles are arranged in parallel with each other; driving means for changing a direction of a rotary member in which the nozzle-installing pipe is provided; and control means for controlling the operation of the driving means.

The automatic sterilizing apparatus further comprises: a plate, rotatable horizontally, supported by a shaft extending upward from an upper portion of the body of the car; a pair of side plates disposed on the plate; and an approximately cylindrical rotary member, approximately cylindrical, disposed between the side plates and supported by a pin so as to be vertically rotatable. The driving means comprises means for rotating the plate horizontally, and means for rotating the rotary member vertically.

The driving means comprises first and second motors rotating in opposite directions; the rotation of an output shaft of the first motor is transmitted to the pin fixed to the rotary member by transmitting means comprising a pulley and a belt; the rotation of an output shaft of the second motor is transmitted to the supporting shaft fixed to the rotary member and rotatably supported by the car by the transmitting means comprising the pulley and the belt; and the control means installed in the car controls the rotation of the first and second motors in opposite directions.

The automatic sterilizing apparatus further comprises: a hose for supplying the disinfectant to the nozzles from the disinfectant-supply tank mounted on the plate. The compressed air-supply means comprises: a compressor installed inside the body of the car; a motor for driving the compressor; a filter, installed over an opening of the body, for supplying clean air to the inside of the body; and a hose for supplying compressed air from the compressor to the nozzles.

The automatic sterilizing apparatus further comprises: a cleaning agent-containing tank for supplying cleaning agent to the nozzles via a hose.

An electromagnetic valve is interposed in the hose for supplying disinfectant and an electromagnetic valve is interposed in the hose for supplying cleaning agent, and the opening and closing of the electromagnetic valves are controlled by the control means.

The nozzle-installing pipe disposed inside the rotary member is annular; and the nozzles are installed about the entire periphery of the nozzle-installing pipe at intervals.

A fan is installed inside the rotary member so as to use air discharged from the fan as a means for scattering droplets of the disinfectant sprayed from the nozzles.

It is preferable to supply hot-air to the nozzles for drying the interior of the nozzle-installing pipe after the interior of the nozzle-installing pipe is washed.

Each of the nozzles comprises a main body including a disinfectant-introducing path and a compressed air-introducing path. A forked adapter comprising twin heads is installed on the main body, and a nozzle chip is mounted on the leading end of each head. In this construction, the disinfectant and compressed air flowing through the disinfectant-introducing path and the compressed air-introducing path provided in each head of the adaptor is mixed with each other and the mixture is jetted from a jetting opening formed on the leading end of each nozzle chip. Droplets of the mixture collide with each other to generate particles, the average diameter of which is 10 $\mu$m or less.

Preferably, disinfectant is sprayed from the nozzle until the air in a space is saturated with droplets of disinfectant. To this end, the control means sets spray the time period depending on the volume of the space so that the spray of the disinfectant is automatically stopped.

In another embodiment, the automatic sterilizing apparatus comprises: a disinfectant-supply tank containing disinfectant; compressed air-supply means; a plurality of nozzles, comprising twin heads, for spraying a mixture of disinfectant supplied from the disinfectant-supply tank and compressed air supplied from the compressed air-supply means in the form of particles, the average diameter of which is 10 $\mu$m or less a nozzle-installing pipe on which the nozzles are installed at intervals and piped into required places of a hospital.

There is provided an automatic sterilizing method for mixing disinfectant and compressed air with each other and jetting the mixture of the disinfectant and compressed air from one or a plurality of nozzles, comprising twin heads, in the form of particles, the diameter of which is 10 $\mu$m or less, such that the disinfectant is sprayed until the air in a space is saturated with droplets.

According to the above-described construction, disinfectant is sprayed from the nozzle in the form of very fine droplets in all directions in the space within a desired place. Thus, bacteria floating in the space can be efficiently sterilized. In addition, after particles float in the space, they stick to ceilings, floors, wall surfaces, and the like, thus wetting them. Therefore, bacteria which have stuck thereto can be efficiently sterilized.

BRIEF DESCRIPTION OF THE DRAWINGS

These and other objects and features of the present invention will become clear from the following description taken in conjunction with the preferred embodiments thereof with reference to the accompanying drawings, in which:

FIG. 1 is a side elevational view showing an automatic sterilizing apparatus mounted on a car according to a first embodiment of the present invention;

FIG. 2 is a rear view of the car of FIG. 1;

FIG. 3A is a front view showing an enlarged rotary portion of the apparatus according to the first embodiment;

FIG. 3B is sectional view in which principal portions of the rotary portions are enlarged;

FIG. 4 is a side view showing the enlarged rotary portion of the apparatus according to the first embodiment;

FIG. 5 is a bottom view of the rotary portion of the apparatus according to the first embodiment;

FIG. 6 is a plan view showing an enlarged nozzle-installing portion of the apparatus according to the first embodiment;

FIG. 7 is a sectional view showing an enlarged nozzle of the apparatus according to the first embodiment;

FIG. 8 is a rear view showing an automatic sterilizing apparatus mounted on a car according to a second embodiment of the present invention;

FIG. 9 is a side view of the car of FIG. 8;

FIG. 10 is a side view of the car, on which a cover plate has been mounted, according to the second embodiment;

FIG. 11 is a front view of the car, on which the cover plate has been mounted, according to the second embodiment;

FIG. 12 is a perspective view showing a sterilizing apparatus according to a third embodiment of the present invention;

FIG. 13 is a front view in which principal portions of the apparatus of FIG. 12 are enlarged;

FIG. 14 is a perspective view showing a method of conducting an experiment;

FIG. 15 is an explanatory view showing the method of conducting the experiment;

FIGS. 16(A)–16(C) are diagrams showing experimental results;

FIGS. 17(A)–17(C) are diagrams showing experimental results; and

FIGS. 18(A)–18(C) are diagrams showing experimental results.

DETAILED DESCRIPTION OF THE INVENTION

Figure 1:
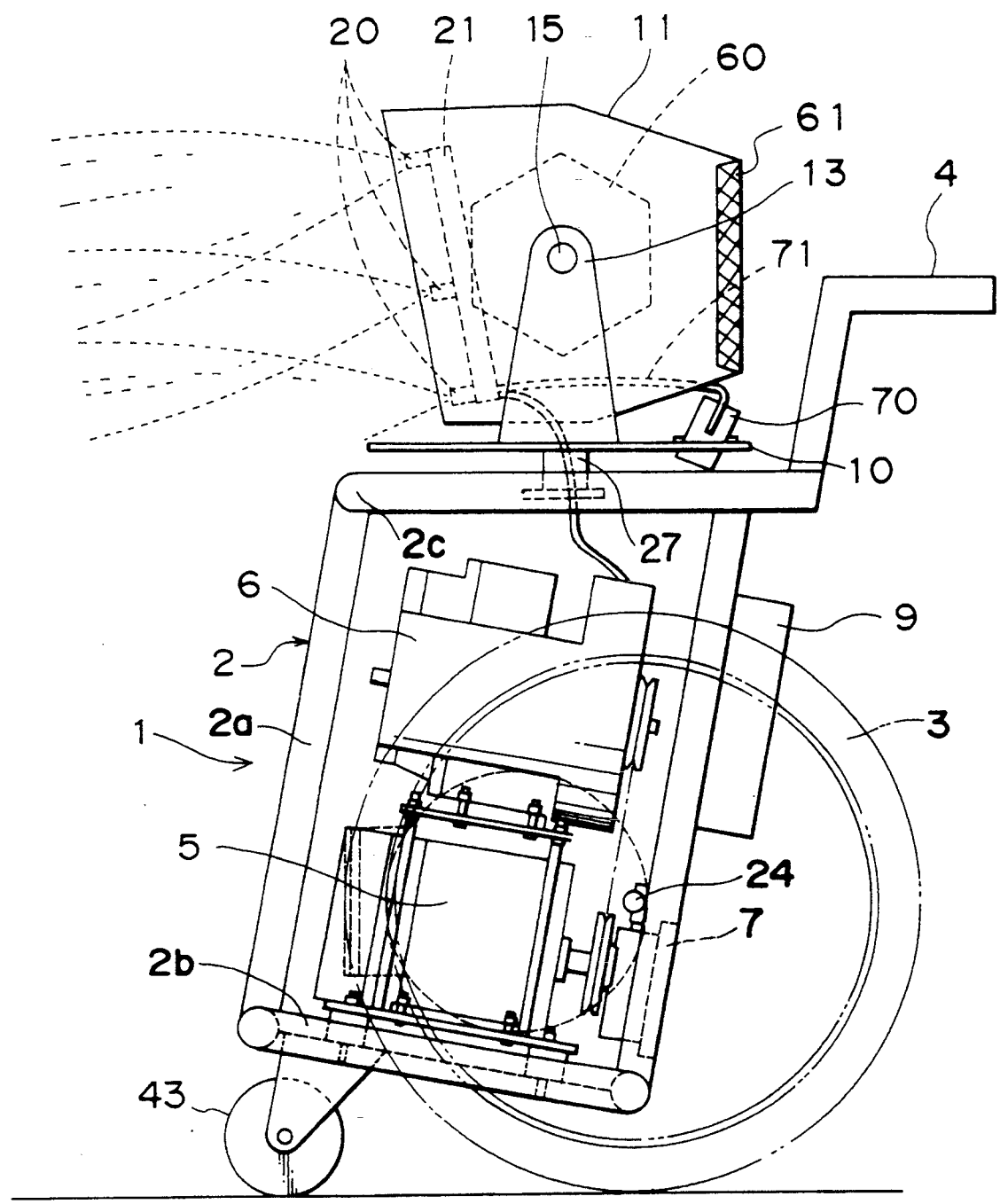
Figure 2:
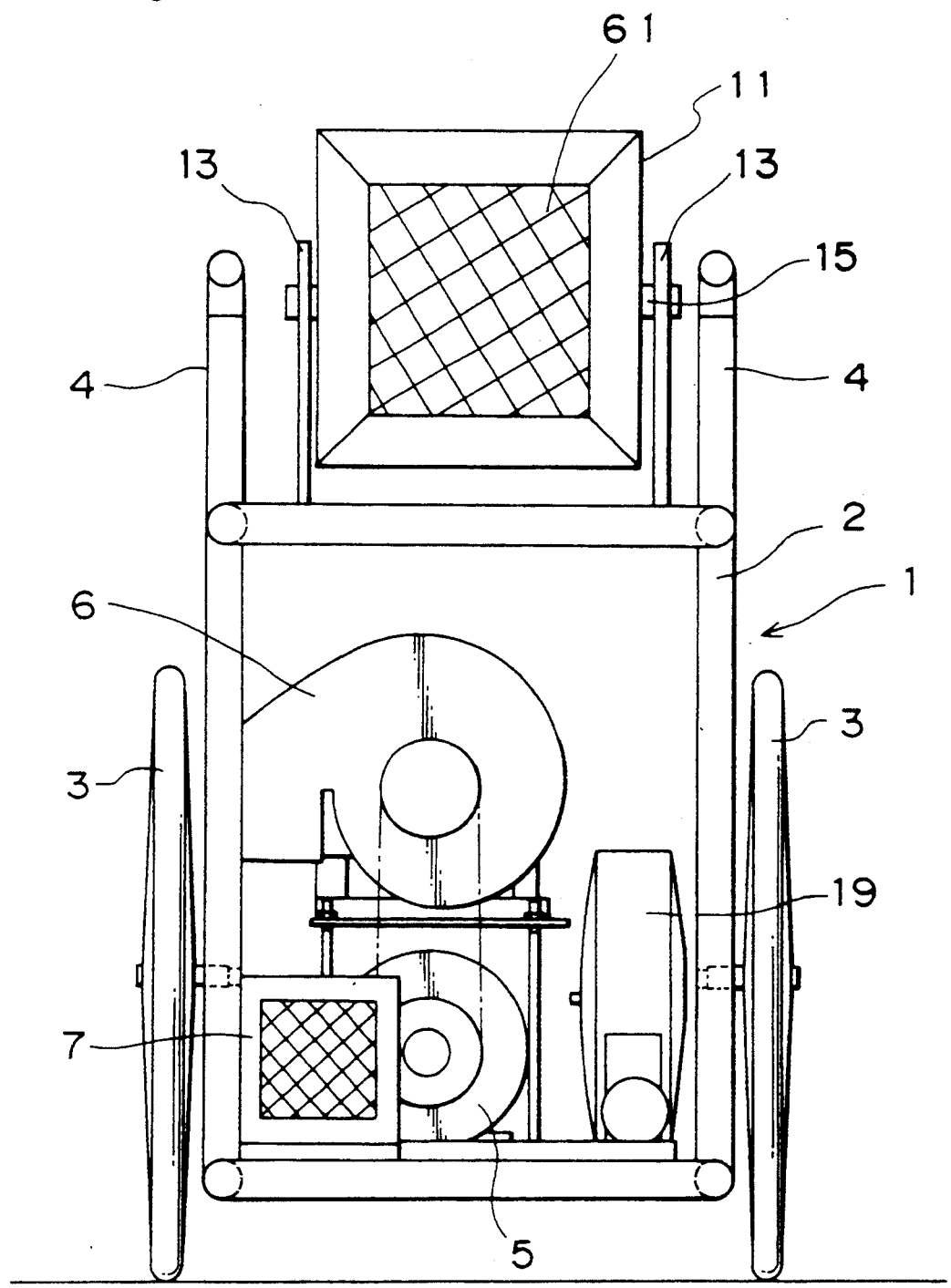

Before the description of the present invention proceeds, it is to be noted that like parts are designated by like reference numerals throughout the accompanying drawings.

An automatic sterilizing apparatus according to a first embodiment of the present invention is described below with reference to FIGS. 1 through 7.

A car (or cart) 1 comprises a pair of wheels 3 disposed at a rear portion of each side of a box-shaped body 2, and a handle 4 disposed at an upper rear portion thereof. The handle 4 is gripped to move the car 1 to a required place.

The body 2 comprises a rectangular frame 2a; a bottom plate 2b fixed to the bottom surface of the frame 2a; an upper plate 2c fixed to the upper surface of the frame 2a; and a cover plate (not shown) removably installed on the periphery of the frame 2a.

The body 2 accommodates a compressor-driving motor 5; a compressor 6 to be driven by the motor 5; a filter 7 for feeding clean air to the compressor 6; a control panel 9; and a cord reel 19. The cover plate is installed on the body 2 after these component parts are mounted inside the body 2. The filter 7 disposed on an opening formed on the cover plate cleans air to be fed into the body 2 closed with the cover plate.

Figure 4:
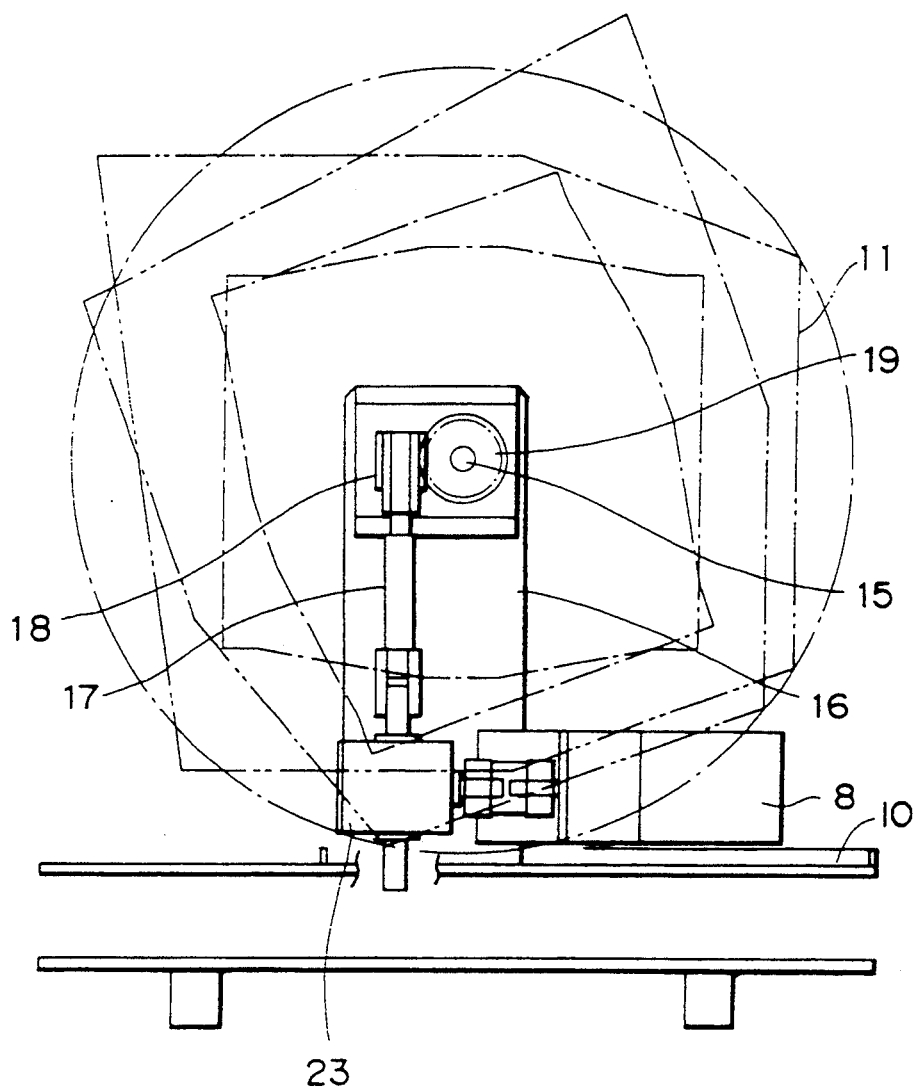
Figure 5:
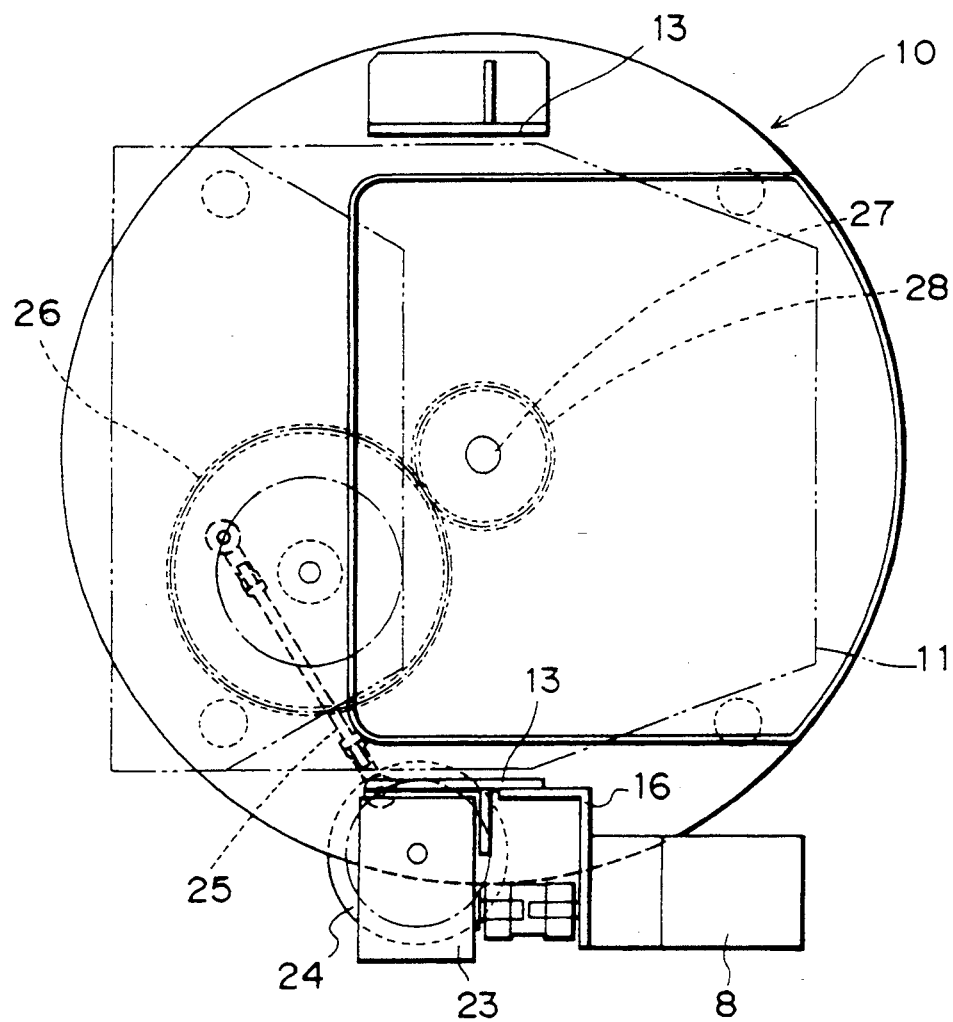

A plate 10 is supported on the upper end of the body 2 so that the plate 10 is rotatable horizontally (i.e. about a vertical axis). As shown in FIGS. 3 through 5, a rotary member (or casing) 11 installed above the plate 10 is rotated vertically (i.e. about a horizontal axis) by a motor 8 mounted on the plate 10. That is, the rotary member 11 is rotatable both horizontally and vertically.

More specifically, referring to FIGS. 3 through 5, a cylindrical supporting shaft 27 is fixed to the center of the circular plate 10. Via a sliding contact member 41, the supporting shaft 27 is inserted into a small-diameter gear 28 fixed to the upper plate 2c of the body 2 via a spacer 38. A compressed air-supply pipe 21A and electric wires are introduced into the rotary member 11 from the body 2 through the cylindrical supporting shaft 27.

A pair of side plates 13 vertically extends from the upper surface of the plate 10. A pin 15 projecting horizontally from each side of the rotary member 11 is supported by the side plate 13 at an upper portion thereof via a bearing 14. The pin 15 supports the rotary member 11 so that the rotary member 11 disposed between the side plates 13 is rotatable vertically.

A frame 16 projects from one of the side plates 13. The motor 8 is installed on a lower portion of the frame 16. Via a bevel gear (not shown) installed inside a gear box 23, the rotation of the output shaft of the motor 8 is transmitted to a rod 17 extending upward from the gear box 23. A worm gear 18 fixed to the upper end of the rod 17 engages a worm wheel 19 fixed to the pin 15 as shown in FIG. 4. In this construction, the rotation of the motor 8 causes the worm wheel 19 to rotate, thus rotating the pin 15 in unison with the worm wheel 19. Consequently, the rotary member 11 rotates vertically.

Via the bevel gear installed inside the gear box 23, the rotation of the output shaft of the motor 8 is also transmitted to a crank 24 projecting downward from the gear box 23. One end of a rod 25 is coupled with the crank 24 and the other end thereof is coupled with a large-diameter gear 26 which is fixed to the plate 10 and positioned in a gap between the plate 10 and the upper plate 2c of the body 2. The large-diameter gear 26 engages the small-diameter gear 28 into which the supporting shaft 27 of the plate 10 is inserted. Since the small-diameter gear 28 is fixed to the upper plate 2c, the large-diameter gear 26 rotates both around the small-diameter gear 28 and on its axis in engagement with the small-diameter gear 28. In this manner, the plate 10 rotates on the supporting shaft 27 horizontally.

The rotation of the rotary member 11 in the vertical direction is varied at a predetermined angle by changing the rotational direction of the motor 8 every predetermined period of time (7.5 minutes in the first embodiment.) In the first embodiment, the rotary member 11 rotates at an angle of 0°→70°→0° in its reciprocating motion.

Similarly, the rotation of the rotary member 11 in the horizontal direction is varied at a predetermined angle by changing the rotational direction of the motor 8 every predetermined period of time of 7.5 minutes. According to the change in the rotational direction of the motor 8, the gear 26 changes its rotational direction at an angle of 0°→55°→0°→55° via the crank 24 and the rod 25 in its reciprocating motion. The above rotational angle of the gear 26 is determined by setting the gear ratio between the gears 26 and 28. In this manner, the rotary member 11 rotates at an angle of 220° (±110°) horizontally in its reciprocating motion. Upon change in the rotational direction of the motor 8, the rotary member 11 makes an angle of 0° or 70° with a vertical line in its vertical rotation and reverses its rotational direction in its horizontal rotation.

The rotation of the rotary member 11 is controlled so that in its vertical and horizontal rotations, it returns to the original position upon completion of the automatic drive.

A limit switch may be used to control the both-way rotation of the motor 8.

A fan 60 is installed inside the rotary member 11 so that air discharged from the fan 60 is used to scatter droplets of disinfectant in a room. A filter 61 is mounted on the rear surface of the rotary member 11.

A disinfectant-containing tank 70 is removably installed on a rear portion of the plate 10.

Figure 3A:
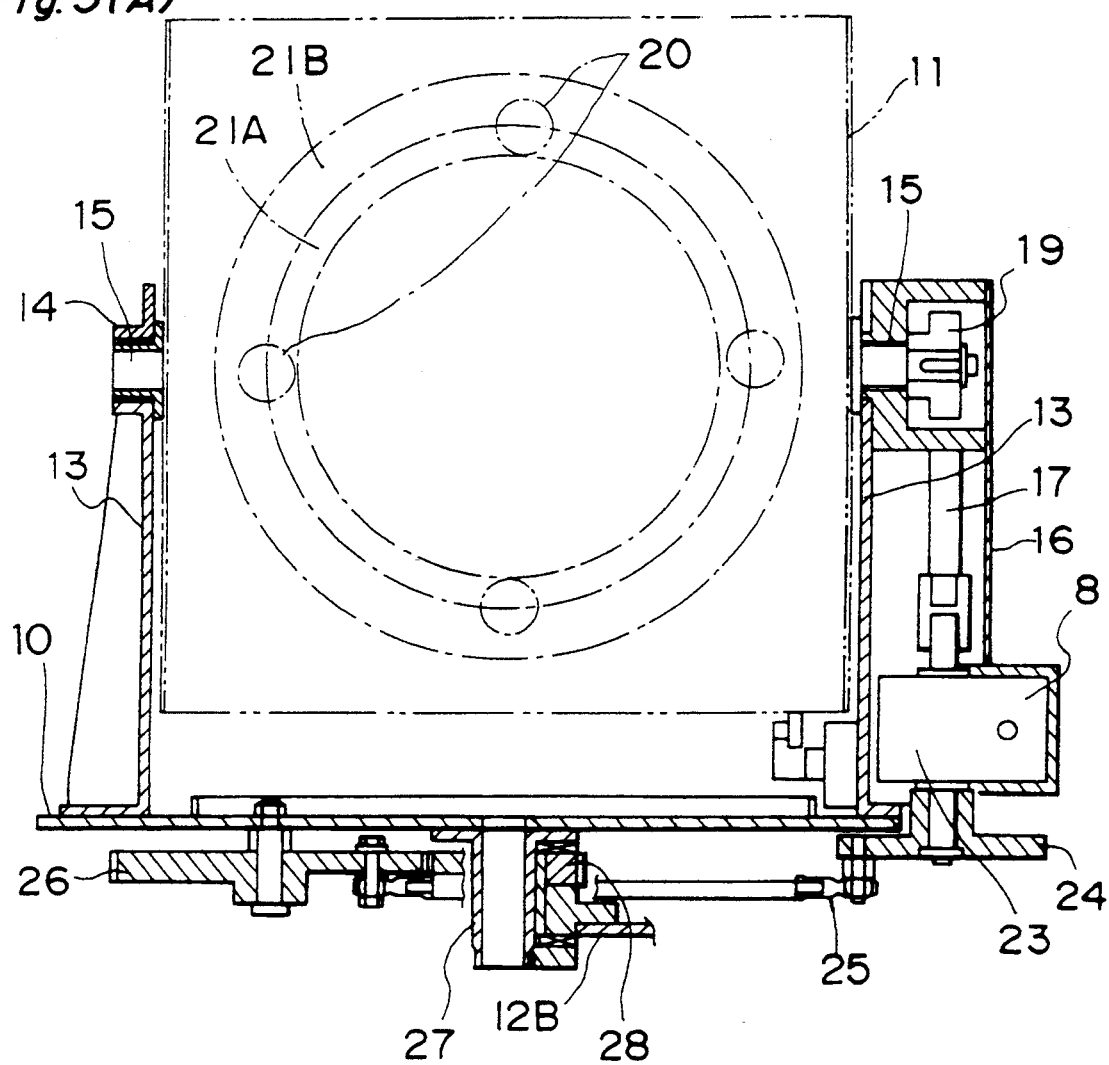
Figure 3B:
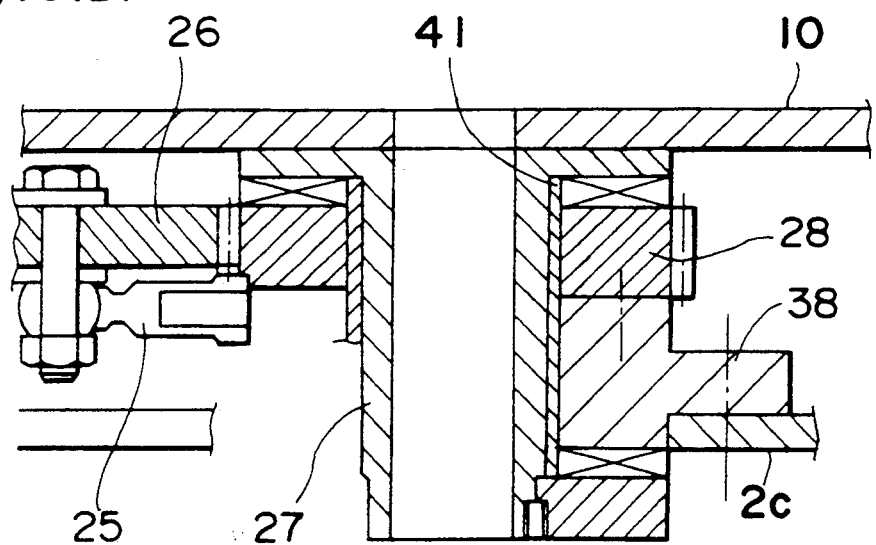

An annular nozzle-installing pipe 21 is mounted on the front side of the rotary member 11 as shown in FIG. 3A. The nozzle-installing pipe 21 comprises a compressed air-supply pipe 21A and a disinfectant-supply pipe 21B adjacent to each other. Disinfectant is supplied from the disinfectant-containing tank 70 to the disinfectant-supply pipe 21B via a hose 71, and compressed air is supplied from the compressor 6 installed inside the body 2 to the compressed air-supply pipe 21A as shown in FIGS. 1 and 3A.

Figure 6:
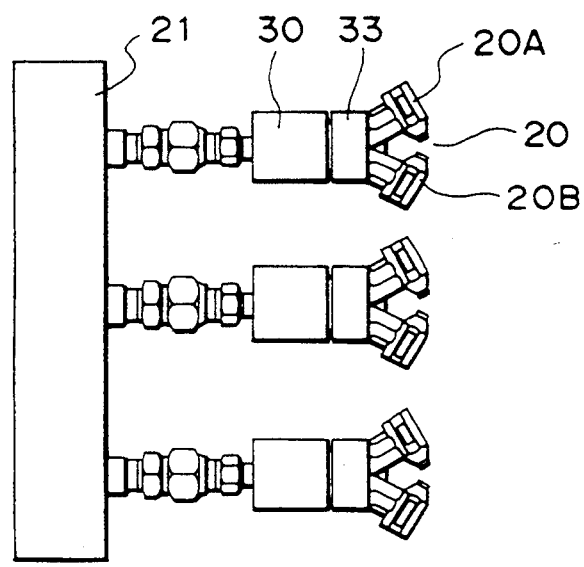
Figure 7:
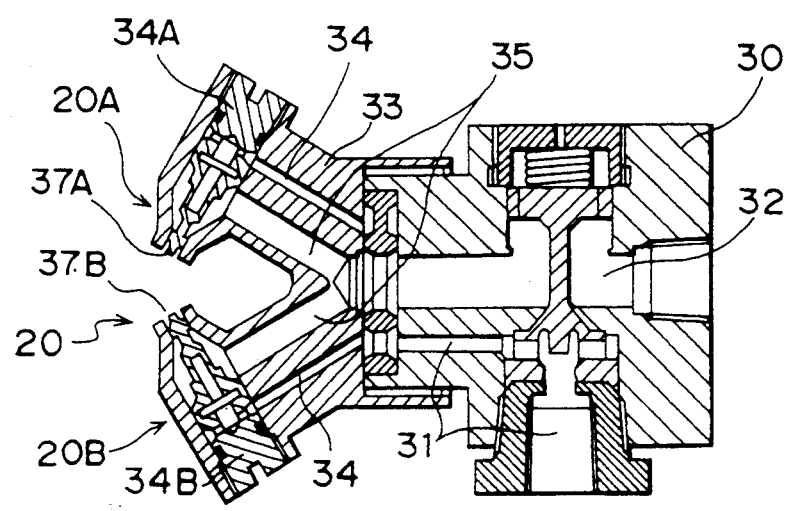
Figure 8:
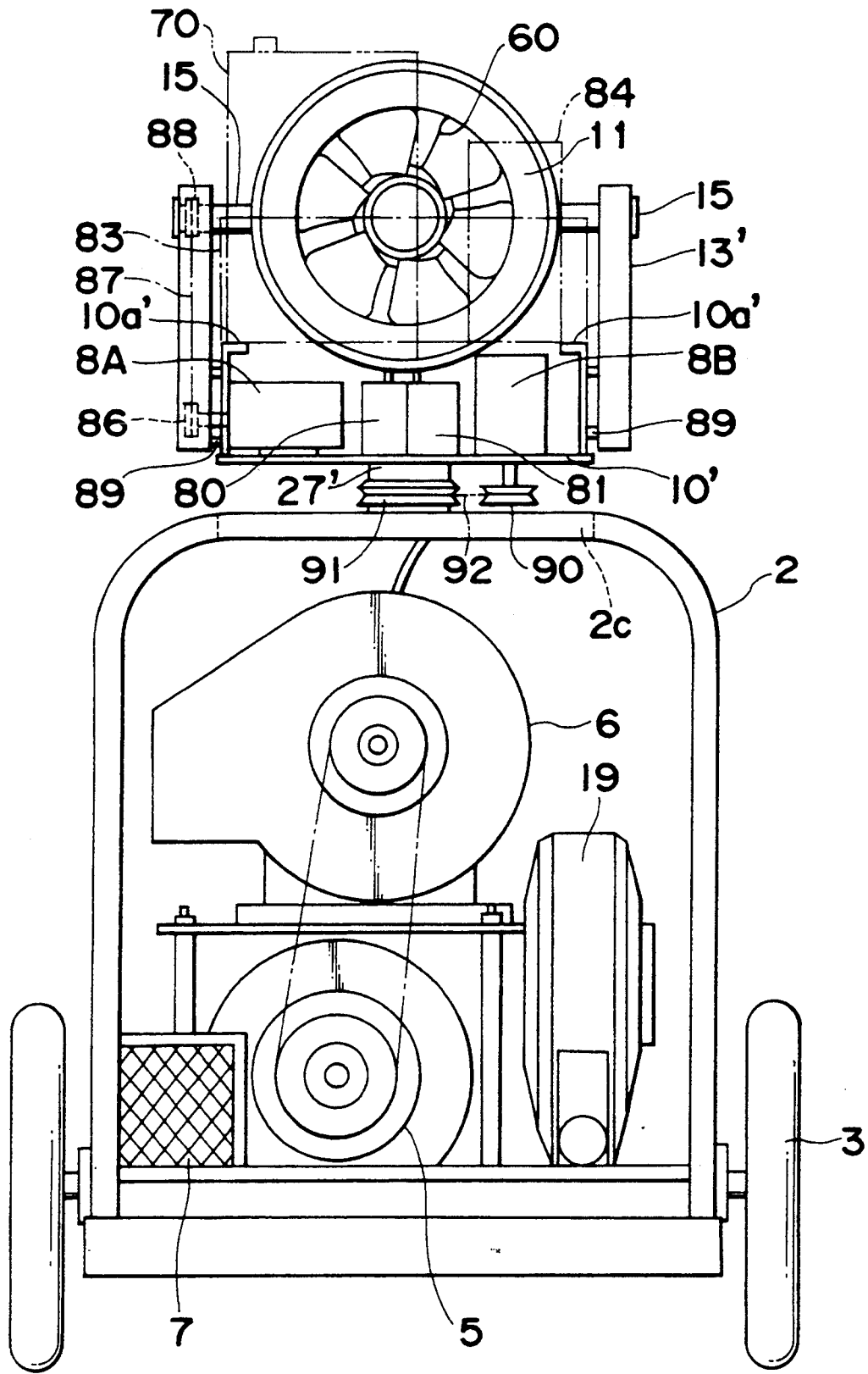
Figure 9:
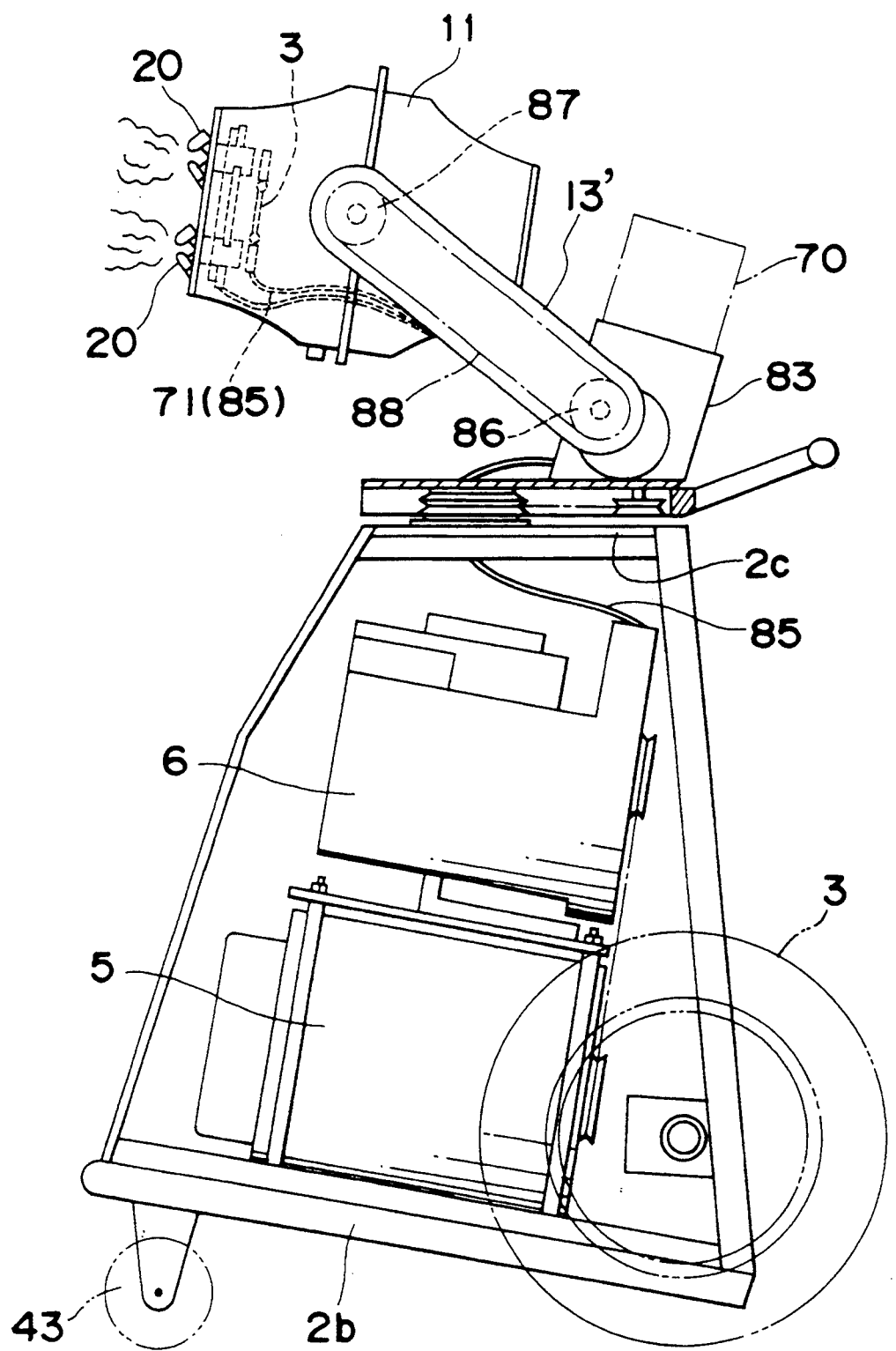

Referring to FIGS. 6 and 7, nozzles 20 comprising a pair of nozzle heads 20A and 20B including jetting openings formed in opposition to each other are installed on the nozzle-installing pipe 21 at regular intervals.

As proposed by the present applicant and disclosed in Japanese Laid-Open Patent Publication No. 62-289257 (U.S. Pat. No. 4,783,008), a forked adapter 33 is installed on a main body 30 comprising a disinfectant-introducing path 31 and a compressed air-introducing path 32, and a pair of nozzle chips 34A and 34B is mounted on both leading ends of the adapter 33, so that the jetting openings 37A and 37B of each of the nozzle heads 20A and 20B are opposed to each other. The adapter 33 comprises paths 34 and 35 communicating the disinfectant-introducing path 31 and the compressed air-introducing path 32 in the main body, respectively. The path 31 is communicated with the disinfectant-supply pipe 21B and the path 32 is communicated with the compressed air-supply pipe 21A The mixture of droplets of disinfectant and compressed air is sprayed from the jetting openings 37A and 37B, opposed to each other, disposed at both leading ends of the adaptor 33.

A control device of the control panel 9 controls the operation of the compressor 6 and that of the motor 8 so as to control the spray direction of the rotary member 11 and spray time period. That is, disinfectant is sprayed from the nozzle 20 for a certain period of time until the air in a room is saturated with droplets of the disinfectant. For example, the spray of disinfectant is stopped after a predetermined period of time according to the volume of a room.

A caster 43 is installed on a front portion of the bottom surface of the body 2.

In sterilizing bacteria by using one car 1, the car 1 is moved into a place, for example, an operation room, and stopped at a center of the room. Then, the spray time period is set by inputting information to the control device. The operation room is closed as soon as the person in charge leaves.

In jetting disinfectant from the nozzle 20, the compressor 6 is driven to jet the mixture of disinfectant and compressed air, with the rotary member 11 rotated by an angle 220° (±110°) horizontally and 70° upward.

In this manner, the mixture can be sprayed in all directions of the operation room without rotating or moving the car 1.

In the nozzle 20, droplets of disinfectant are atomized by ultrasonic waves and shearing force. That is, the disinfectant is sheared finely by the compressed air, when the disinfectant is mixed with the compressed air supplied from the compressor 6. The compressed air together with the fine droplets of disinfectant sheared are jetted out by ultrasonic waves from the jetting openings 37A and 37B opposed to each other and mix with atomized droplets of the disinfectant. Owing to generated ultrasonic waves of 20,000 to 35,000 Hertz, atomized droplets and compressed air jetted from the two openings 37A and 37B repeatedly collide with each other at a predetermined angle. In this manner, atomized droplets become finer and the diameter thereof become uniform.

The diameter of each fine droplet sprayed from the nozzle 20 10 μm or smaller.

The spray of fine droplets of disinfectant is continued until the air in the room is saturated with droplets. The spray time period is set by means of the control panel 9.

Since the diameter of each fine droplet sprayed from the nozzle 20 10 μm or smaller, droplets stay in the air for a long time. Disinfectant is sprayed until the air in the room is saturated with droplets. Thus, bacteria floating in the space can be efficiently sterilized.

Since disinfectant is sprayed until the air in the room is saturated with droplets of the disinfectant, disinfectant droplets stick to the ceiling and wall of the room, the top and bottom surfaces of medical equipment and the like, thus wetting them. Therefore, bacteria which have stuck thereto can be efficiently sterilized.

After they float in the space, droplets fall by dead load, thus wetting the floor and sterilizing bacteria which have stuck to the surface of the floor.

In the automatic sterilizing apparatus, hot air discharged from a drier provided on the compressor 6 is automatically applied to the path between the nozzle 20 and the nozzle-installing pipe 21A after a predetermined amount of disinfectant is sprayed, to keep the path clean and dry. The hot air has a temperature of more than 60° C.

The fan 60 mounted inside the rotary member 11 causes the flight distance of droplets to be long, thus scattering droplets uniformly in the space of the room and making them collide with the floor and the ceiling. Consequently, bacteria which have stuck to the floor and the ceiling can be efficiently sterilized.

After a predetermined quantity of disinfectant is sprayed, the inside of the nozzle 20 is automatically washed with sterile water.

An automatic sterilizing apparatus according to the second embodiment of the present invention is described below with reference to FIGS. 8 through 11 showing a movable car. The second embodiment is different from the first embodiment in that the rotary member 11 is rotated vertically by a motor 8A installed on a plate 10' and horizontally by a motor 8B installed thereon.

That is, the supporting shaft 27' is rotatably supported on the upper plate *2c* fixed to the upper surface of the frame *2a*, and the plate 10' is fixed to the upper end of the supporting shaft 27'.

The first and second motors 8A and 8B are installed on a rear portion of the upper surface of the plate 10', and electromagnetic valves 80 and 81 are disposed between the first and second motors 8A and 8B.

A pair of box-installing frames **10*a*' is vertically disposed at the periphery of the first and second motors 8A and 8B. A tank-accommodating box 83 is installed on the box-installing frame 10*a***.

The tank-accommodating box 83 accommodates the disinfectant-containing tank 70 and a cleaning agent-containing tank 84. One end of supply hose 71 is diverged into two hoses, one of which is connected with the tank 70 and the other of which is connected with the tank 84. The other end of the hose 71 is connected with the disinfectant-introducing path of the nozzle-installing pipe installed in the rotary member 11. One end of a hose 85 is connected with the compressor 6 and the other end of the hose is connected with the compressed air-introducing path. The electromagnetic valves 80 and 81 are interposed between the hoses 71 and 85.

A pair of side plates 13' is fixed to the outer surface of the frame **10*a*' via pins 89 at first ends. The fixed to both ends of the rotary member 11 are rotatably installed on the other end of each of the side plates 13'. A pulley 86 fixed to the output shaft of the first motor 8A projecting horizontally outward is accommodated inside one of the side plates 13'. A belt 87 is spanned between the pulley 86 and a pulley 88 fixed to the pin 15. In this construction, due to the rotation of the first motor 8A**, the rotary member 11 is rotated vertically via the pulley 86, the belt 87, the pulley 88, and the pin 15. The rotational angle of the rotary member 11 is in the range of −30° to 50°.

The output shaft of the second motor 8B projects downward therefrom. A pulley 90 is fixed to the lower end of the output shaft of the second motor 8B, and a pulley 91 is fixed to the supporting shaft 27' rotatably supported by the body 2 and fixed to the plate 10'. A belt 92 is spanned between the pulleys 90 and 91. In this construction, as a result of the rotation of the second motor 8B, the supporting shaft 27' is rotated via the pulley 90, the belt 92, and the pulley 91. Consequently, the plate 10' rotates 360° horizontally. The rotational angle of the plate 10' can be set by controlling the time period in which the second motor 8B is rotated in one direction (clockwise or counterclockwise, and the mounting position of the limit switch.

Figure 10:
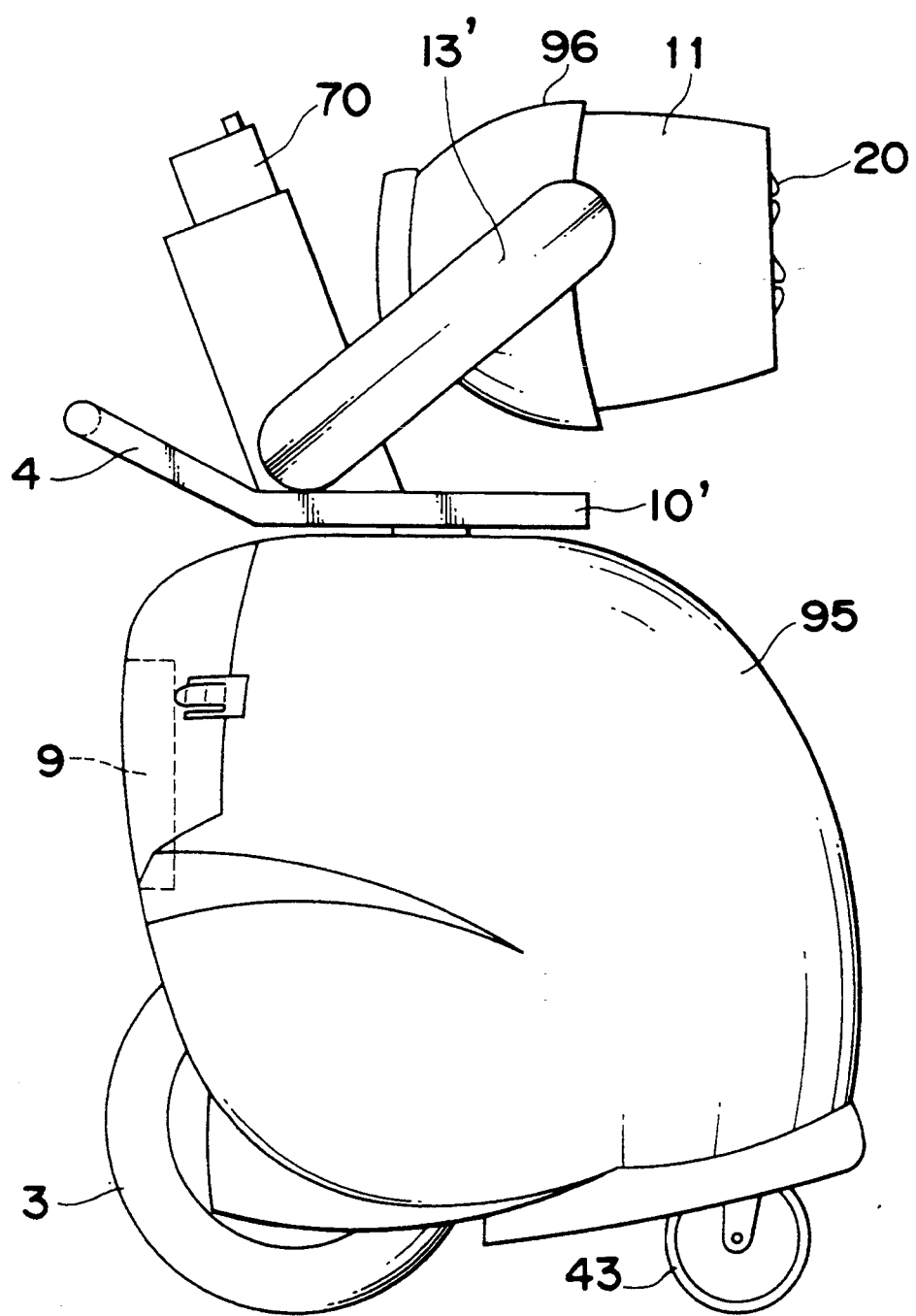
Figure 11:
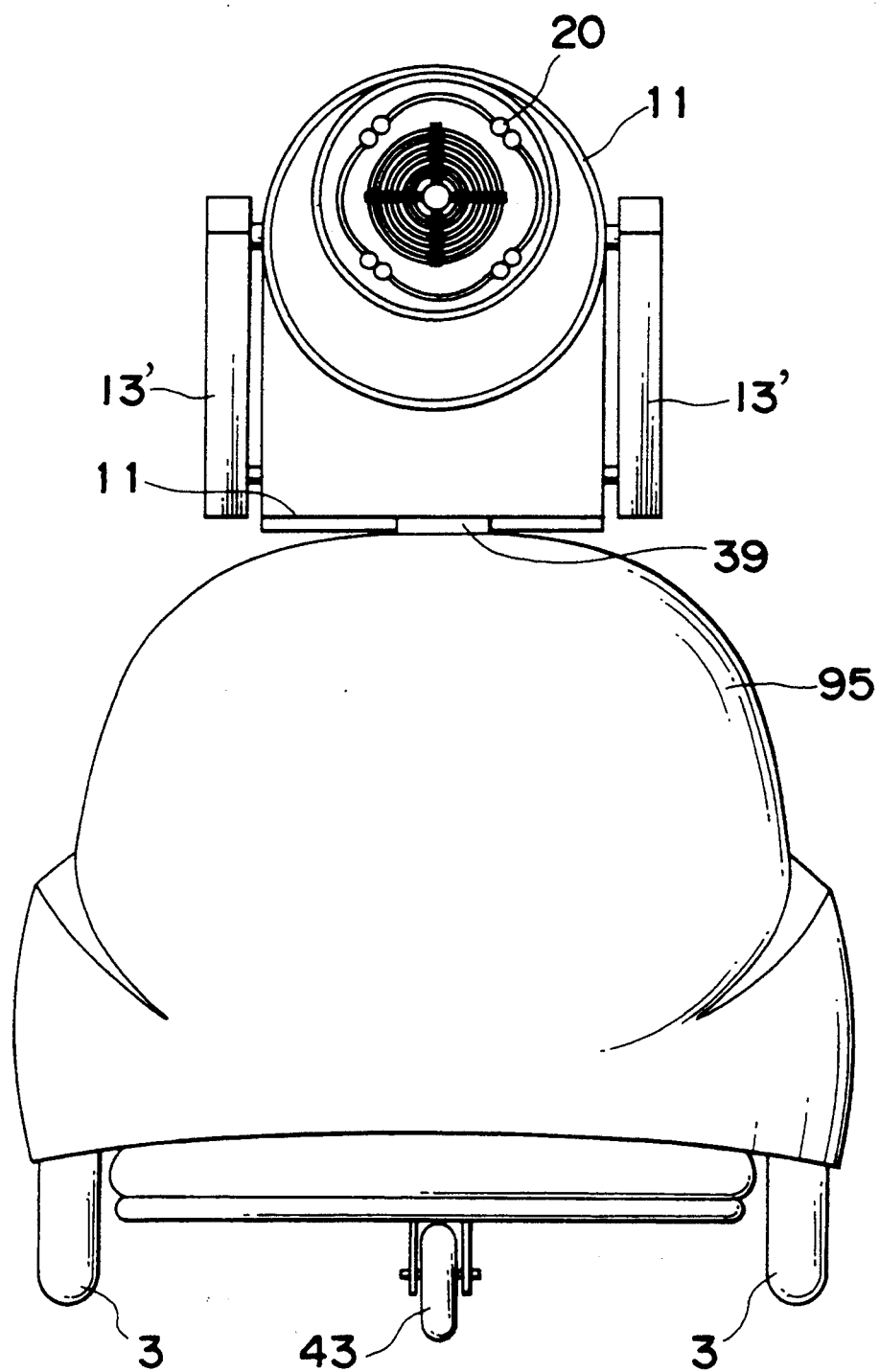

Similarly to the first embodiment, the body 2 accommodates the compressor 6, the compressor-driving motor 5, and the cord reel 19. After these component parts are installed inside the body 2, cover plate 95 is mounted on the frame of the body 2 as shown in FIGS. 10 and 11. A control box 9 is mounted on the inner face of the cover plate 95 disposed on the rear side of the frame 2. The handle 4 of the car 1 extends from the rear end of the plate 10'. A cover 96 is installed on the rotary member 11.

Since the remaining construction is similar to that of the first embodiment, the description thereof will be omitted.

The operation of the second embodiment is also similar to that of the first embodiment except that the rotational angle of the rotary member 11 according to the second embodiment is larger than that of rotary member 11 according to the first embodiment because one of the two motors is used to rotate the rotary member 11 horizontally and the other motor is used to rotate the rotary member 11 vertically. That is, the rotary member 11 can be rotated 360° horizontally and a larger angle vertically through angles at which the body 2 faces downward.

Figure 12:
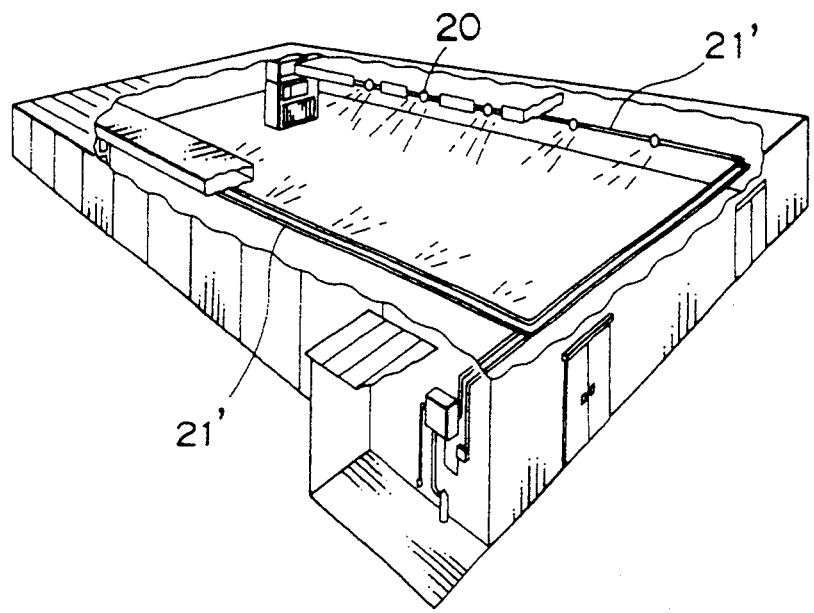
Figure 13:
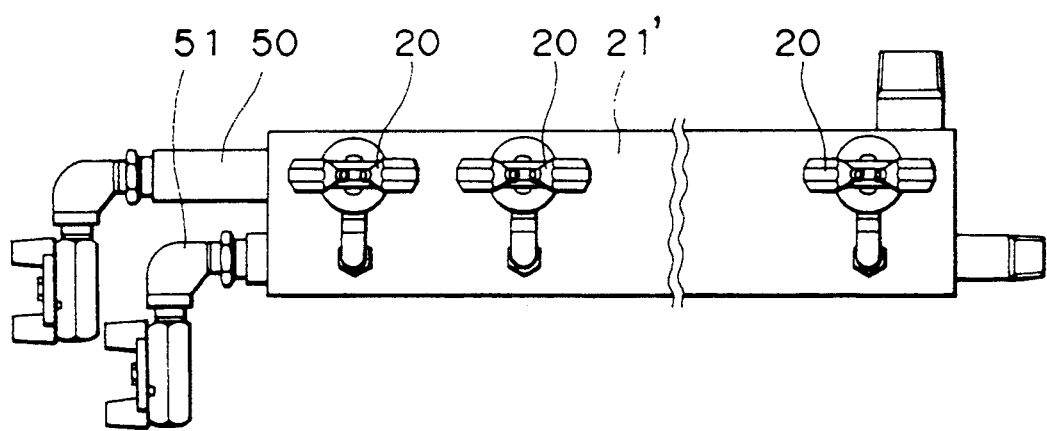

A third embodiment of the present invention is described below with reference to FIGS. 12 and 13. As shown in FIGS. 12 and 13, a nozzle-installing pipe 21' is disposed in a required place, for example, a ceiling of a hospital. The nozzles 20 are installed on the nozzle-installing pipe 21' at intervals. The diameters of particles of disinfectant sprayed from the nozzle 20 are 10 μm or less.

A disinfectant-supply pipe 50 and a compressed air-supply pipe 51 are connected with the nozzle-installing pipe 21'. The disinfectant supply pipe 50 and the compressed air-supply pipe 51 are connected with a disinfectant-containing tank and a compressor, respectively, so as to jet disinfectant mixed with compressed air from the nozzle 20. The directions of the nozzles are adjusted to flow disinfectant by convection so as to wet a ceiling, wall, and floor of a room uniformly.

No manual labor is required to spray disinfectant from the nozzles 20 of the nozzle-installing pipe 21'.

Disinfectant is sprayed from the nozzles 20 until the ambient air in the room is saturated with droplets of the disinfectant. To this end, the apparatus is provided with means for detecting a saturated condition. For example, a black disk having a diameter of 30 cm is hung at a position two meters apart from a window of the room. The saturated condition can be detected when the disk cannot be seen from outside.

EXPERIMENT

The following experiments were conducted to demonstrate the effects of the sterilizing operation of the spraying method according to the present invention.

Figure 14:
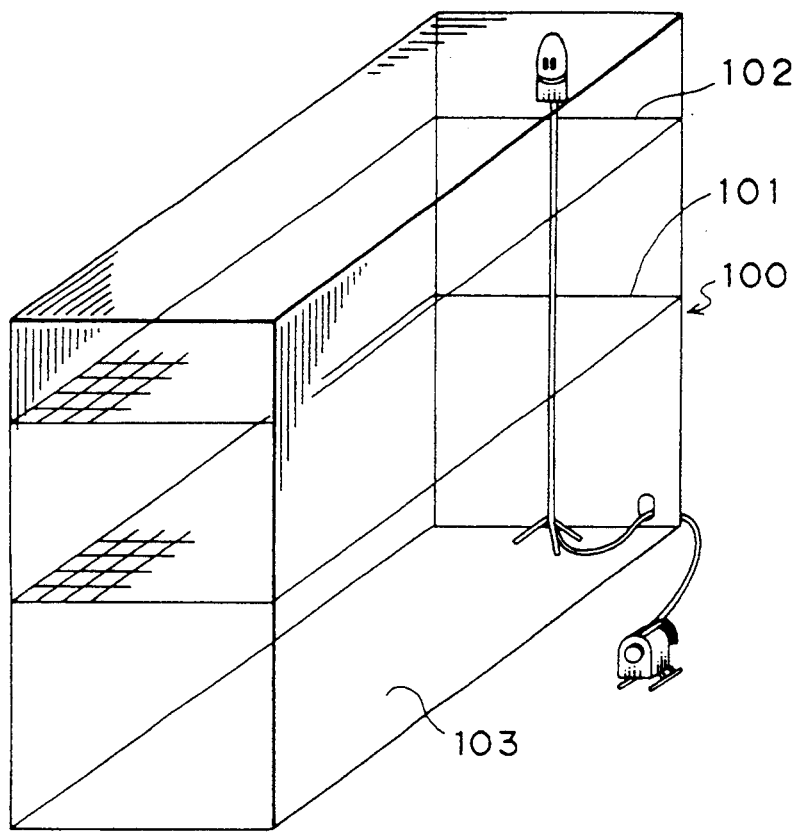

As shown in FIG. 14, a test booth 100 of 2 m × 1.2 m × 2 m was prepared. The booth 100 comprises a 0.9 m-high intermediate shelf 101, a 1.6 m-high upper shelf 102, and a floor 103. Petri dishes 105 having a culture medium were placed on the upper shelf 102, the intermediate shelf 101, and the floor 103, with bacteria put on the petri dishes 105. Disinfectant was sprayed into the booth 100 from the nozzle 20 from the height of 1.8 m with the booth 100 covered with a sheet. The air in the booth 100 was saturated with disinfectant.

Figure 15:
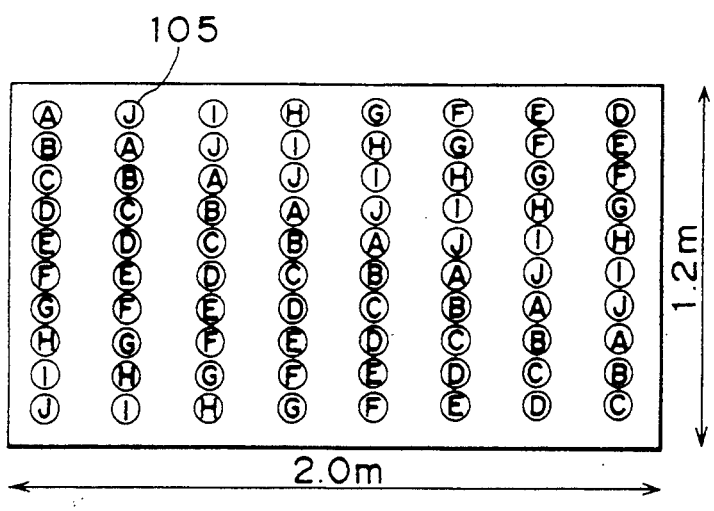

As shown in FIG. 15, 80 (8 × 10) pieces of petri dishes 105 were put on each of the shelves, with 10 kinds of bacteria put thereon. Petri dishes having the same alphabet letter designation (same kind of bacteria) thereon were arranged diagonally.

That is, letters (A) through (J) denote the following bacteria: A: Methicillin Resistant Staphylococcus aureus, B: Enterococcus, C: Colibacillus, D: Serratia, E: Pseudomonas aeruginosa, F: Pseudomonos cepacia, G: Acinetobacter, H: Candida, I: Methicillin Resistant Staphylococcus aureus (standard strain), J: Pseudomonas aeruginosa (standard strain).

The kind of disinfectant, the concentration thereof, and time duration of spraying were varied. After disinfectant was sprayed in the booth 100, bacteria were cultured at 37° for 24 to 48 hours to observe the growth degree of bacteria.

Figure 16C:
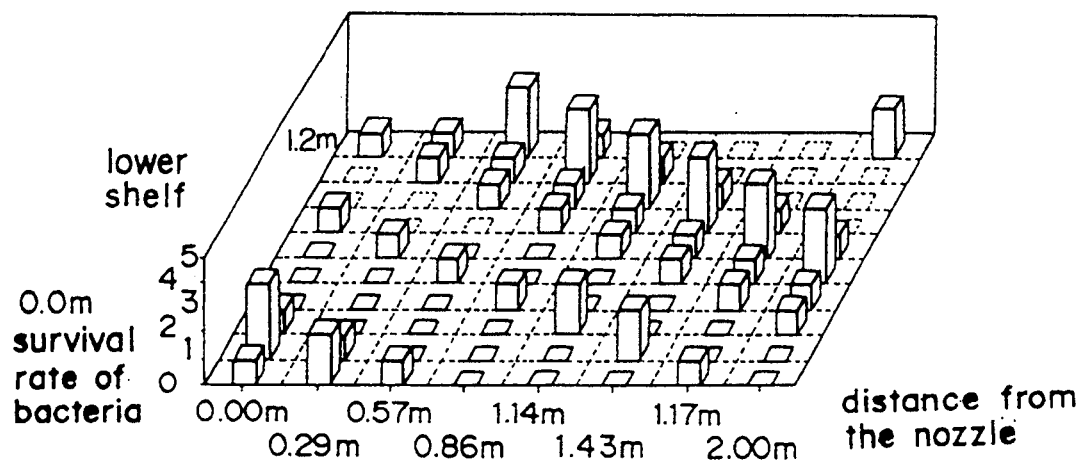
Figure 18C:
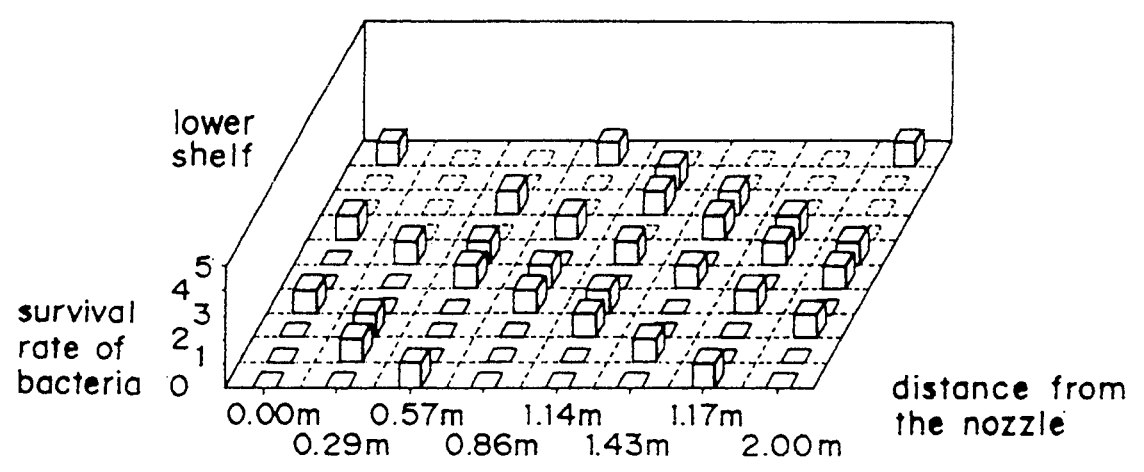

The results are shown in FIGS. 16 through 18.

Figure 17A:
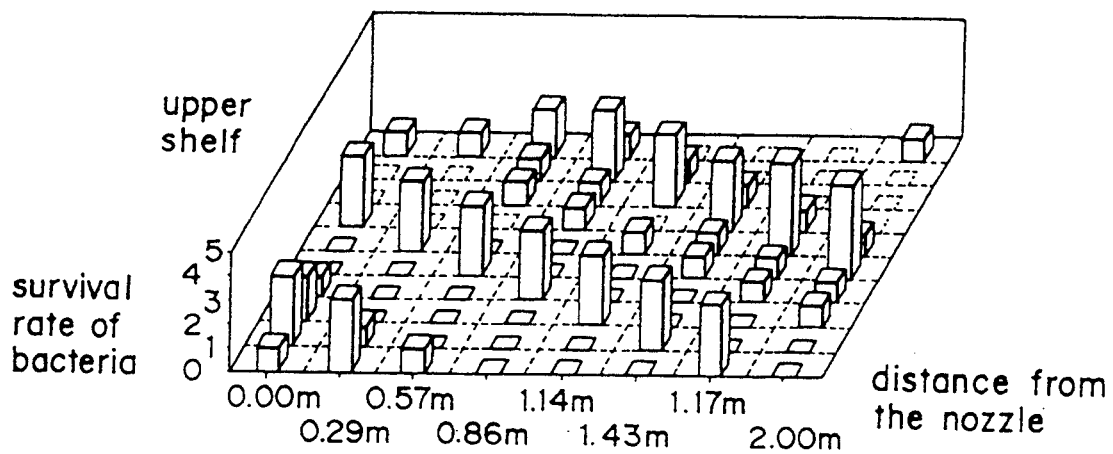

Osban (trade mark of Beuzalkonium Chloride) was used as the disinfectant. Concentration of Osban: 0.20%. Spray period of time: five minutes. The diameters of particles of droplets: $d_{32}$ 10 μm. The results are shown in FIGS. 17(a), 17(b) and 17(c) for the upper, intermediate and lower shelves, respectively.

Spray period of time was changed to eight minutes with other conditions unvaried. The results are shown in FIGS. 17(a), 17(b) and 17(c) for the upper, intermediate and lower shelves, respectively.

There was little difference in bacteria-sterilizing effect between the five minute test and the eight minute test. That is, sterilizing effects can be obtained irrespective of a spray time period so long as the disinfectant is sprayed for more than a certain period of time. Therefore, disinfectant can be efficiently consumed.

The sterilizing effect was more favorable in the lower shelf than in the upper shelf, but there was not a great difference therebetween. This indicates that the method and apparatus of the present invention was effective especially for sterilizing bacteria floating in the space.

FIG. 18 shows the results of the experiment in which isodine (trade mark of Povidone-Iodine) was used as disinfectant, concentration thereof: 1.0%, spray time period: eight minutes, and diameter of particles of droplets was $d_{32} = 10$ μm.

The experiment indicates that a greater concentration brought about a favorable sterilizing effect; that bacteria was sterilized to almost the same degree in each shelf; and that bacteria floating in the space were suitably sterilized.

As apparent from the foregoing description, according to the method and apparatus according to the present invention, disinfectant is sprayed in particles, the diameter of which is less or less. Therefore, bacteria floating in the space of a room can be efficiently sterilized. In addition, after particles float in the space, they stick to ceilings, floors, wall surfaces, medical equipment, and the like, thus wetting them. Therefore, bacteria which have stuck to back surfaces of medical equipment and the like can be efficiently sterilized.

The automatic sterilizing apparatus according to the present invention is automatically operated. Therefore, the mixture of disinfectant and compressed air can be sprayed in all directions of a room with the car stopped at a required place. In addition, a person in charge of spraying the disinfectant can be prevented from being infected with bacteria.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. An automatic sterilizing apparatus comprising:
   a cart;
   a disinfectant supply tank mounted on said cart;
   a compressed air supply mounted on said cart;
   a support plate rotatably mounted on said cart for rotation about a vertical axis;
   a pair of side plates mounted on and extending upwardly from said support plate;
   a rotary casing interposed between and rotatably mounted to said side plates for rotation about a horizontal axis;
   a nozzle-installing pipe mounted to and disposed in said rotary casing, said nozzle-installing pipe being operably connected with said disinfectant supply tank and said compressed air supply;
   a plurality of nozzles arranged on said nozzle-installing pipe and constituting means for spraying a mixture of disinfectant supplied from said disinfectant supply tank and compressed air supplied from said compressed air supply in the form of disinfectant particles having an average diameter of 10 $\mu$m or less, each of said nozzles comprising twin nozzle heads;
   driving means mounted on said cart for rotating said support plate about said vertical axis and for rotating said rotary casing about said horizontal axis; and
   control means for controlling operation of said driving means.

2. An automatic sterilizing apparatus as recited in claim 1, wherein
   said driving means comprises a reversible motor, a first transmission means for transmitting drive of said reversible motor to said support plate to rotate said support plate about said vertical axis, and a second transmission means for transmitting drive of said reversible motor to said rotary casing to rotate said rotary casing about said horizontal axis.

3. An automatic sterilizing apparatus as recited in claim 2, wherein
   a support shaft is provided, is concentric with said vertical axis and rotatably mounts said support plate to said cart;
   said first transmission means comprises a gear fixed to said support plate, and a means for transmitting rotary output of said reversible motor to said gear to rotate said support plate about said vertical axis; and
   said second transmission means comprises a pin connected to said rotary casing and rotatably mounting said rotary casing to said side plates, and means for transmitting rotary output of said reversible motor to said pin to rotate said pin about said horizontal axis.

4. An automatic sterilizing apparatus as recited in claim 1, wherein
   said driving means comprises first and second reversible motors, a first transmission means for transmitting drive of said first reversible motor to said support plate to rotate said support plate about said vertical axis, and a second transmission means for transmitting drive of said second reversible motor to said rotary casing to rotate said rotary casing about said horizontal axis.

5. An automatic sterilizing apparatus as recited in claim 4, wherein
   said first transmission means comprises a first pulley mounted to said support plate and concentric with said vertical axis, a second pulley mounted to an output shaft of said first reversible motor, and a belt trained about said first and second pulleys; and
   said second transmission means comprises a third pulley mounted to said rotary casing and concentric with said horizontal axis, a fourth pulley mounted to an output shaft of said second reversible motor, and a belt trained about said third and fourth pulleys.

6. An automatic sterilizing apparatus as recited in claim 1, wherein
   said cart comprises a cart body with an enclosed inside portion and an opening into said inside portion;
   said compressed air supply comprises a compressor mounted on said inside portion of said cart body, a motor for driving said compressor, a filter mounted over said opening of said cart body for filtering air passing through said opening, and a hose connecting an output of said compressor with said nozzle-installing pipe.

7. An automatic sterilizing apparatus as recited in claim 6, wherein
   said cart body comprises a frame constructed of rods, a bottom plate fixed to a bottom end of said frame, an upper plate fixed to an upper end of said frame, and a cover plate covering side portions of said frame;
   said compressor is supported on said bottom plate; and
   a control panel is mounted on said cover plate, said control panel accommodating said control means.

8. An automatic sterilizing apparatus as recited in claim 1, further comprising
   a cleaning agent tank mounted on said support plate; and
   a hose connecting said cleaning agent tank to said nozzle-installing pipe.

9. An automatic sterilizing apparatus as recited in claim 1, further comprising
   a fan mounted in said rotary casing for discharging air to scatter droplets of disinfectant sprayed from said nozzles.

10. An automatic sterilizing apparatus as recited in claim 1, wherein
each of said nozzles comprises:
a main body having a disinfectant-introducing path and a compressed air-introducing path therein;
a forked adaptor mounted on said main body, said forked adaptor comprising twin nozzle heads, each of which includes a disinfectant-introducing path and a compressed air-introducing path respectively connected with said disinfectant-introducing path and said compressed air-introducing path of said main body, each of said nozzle heads including a jetting opening at a leading end thereof;
a nozzle chip mounted in each of said twin nozzle heads and constituting a means for mixing disinfectant and compressed air respectively introduced through said disinfectant-introducing path and said compressed air introducing path of said nozzle heads, and for jetting the mixture from said jetting openings; and
wherein said jetting openings of said forked adaptor are opposed to one another such that said forked adaptor constitutes a means for causing the mixture jetted from one of said twin nozzles heads to collide with the mixture jetted from the other of said twin nozzle heads to generate the disinfectant particles having an average diameter of 10 $\mu$m or less.

11. An automatic sterilizing apparatus comprising
a disinfectant supply,
a compressed air supply,
a nozzle-installing pipe fluidically connected with said disinfectant supply and said compressed air supply and being constructed and arranged to be mounted at a predetermined location in a hospital room, and
a plurality of nozzles mounted on said nozzle-installing pipe at regular intervals, each of said nozzles comprising:
a main body having a disinfectant-introducing path and a compressed air-introducing path therein;
a forked adaptor mounted on said main body, said forked adaptor comprising twin nozzle heads, each of which includes a disinfectant-introducing path and a compressed air-introducing path respectively connected with said disinfectant-introducing path and said compressed air-introducing path of said main body, each of said nozzle heads including a jetting opening at a leading end thereof;
a nozzle chip mounted in each of said twin nozzle heads and constituting a means for mixing disinfectant and compressed air respectively introduced through said disinfectant-introducing path and said compressed air-introducing path of said nozzle head, and for jetting the mixture from said jetting opening; and
wherein said jetting openings of said forked adaptor are opposed to one another such that said forked adaptor constitutes a means for causing the mixture jetted from one of said twin nozzles heads to collide with the mixture jetted from the other of said twin nozzle heads to generate disinfectant particles having an average diameter of 10 $\mu$m or less, so as to saturate ambient air in the hospital room with said disinfectant particles.

12. An automatic sterilizing apparatus as recited in claim 11, further comprising
a mounting structure, said nozzle-installing pipe being mounted on said mounting structure; and
wherein said mounting structure comprises a ceiling of the hospital room.

* * * * *